United States Patent
Homola et al.

(10) Patent No.: US 8,094,316 B1
(45) Date of Patent: Jan. 10, 2012

(54) SURFACE PLASMON RESONANCE COUPLER AND DISPERSER SENSOR

(75) Inventors: Jiri Homola, Prague (CZ); Marek Piliarik, Prague (CZ); Ivo Tichy, Jaroměř (CZ); Milan Vala, Hranice (CZ); Pavel Adam, Doubravnik (CZ); Jan Hepnar, Přerov 1-Město (CZ); Karel Chadt, Velvary (CZ)

(73) Assignee: Institute Of Photonics And Electronics AS CR, V.V.I., Prague (CZ)

( * ) Notice: Subject to any disclaimer, the term of this patent is extended or adjusted under 35 U.S.C. 154(b) by 246 days.

(21) Appl. No.: 12/464,823

(22) Filed: May 12, 2009

Related U.S. Application Data (60) Provisional application No. 61/052,578, filed on May 12, 2008.

(51) Int. Cl.
*G01N 21/55* (2006.01)

(52) U.S. Cl. ........................ 356/445; 356/446

(58) Field of Classification Search .......... 356/445–448; 436/172, 527, 524; 422/82.05, 82.11
See application file for complete search history.

(56) References Cited

U.S. PATENT DOCUMENTS

| | | | |
|---|---|---|---|
| 4,915,482 A | | 4/1990 | Collins et al. |
| 5,023,053 A | * | 6/1991 | Finlan ........................ 422/82.05 |
| 5,313,264 A | * | 5/1994 | Ivarsson et al. ................. 356/73 |
| 5,455,178 A | | 10/1995 | Fattinger |
| 5,598,267 A | * | 1/1997 | Sambles et al. ................ 356/369 |
| 5,846,843 A | * | 12/1998 | Simon ............................ 436/527 |
| 6,100,991 A | * | 8/2000 | Challener ...................... 356/445 |
| 6,625,336 B2 | * | 9/2003 | Challener et al. ................ 385/12 |
| 6,646,744 B2 | * | 11/2003 | Pedersen et al. ............... 356/445 |
| 6,714,303 B2 | * | 3/2004 | Ivarsson ........................ 356/445 |
| 6,738,141 B1 | * | 5/2004 | Thirstrup ...................... 356/445 |
| 7,233,391 B2 | * | 6/2007 | Schermer et al. ............. 356/246 |
| 7,973,933 B2 | | 7/2011 | Homola et al. |
| 2004/0218184 A1 | | 11/2004 | Jorgenson et al. |
| 2005/0079635 A1 | | 4/2005 | Norman |
| 2007/0081163 A1 | * | 4/2007 | Liang et al. .................... 356/445 |
| 2009/0323073 A1 | * | 12/2009 | Luber et al. .................... 356/448 |

FOREIGN PATENT DOCUMENTS

| | | |
|---|---|---|
| EP | 1 424 549 | 6/2004 |
| JP | 2002-357542 | 12/2002 |
| WO | 2003014711 | 2/2003 |

OTHER PUBLICATIONS

Jory et al., "Development of a Prototype Gas Sensor Using Surface Plasmon Resonance on Gratings," Sensors and Actuators B, vol. 17, pp. 203-209 (1994).

Dostalek et al., "Rich Information Format Surface Plasmon Resonance Biosensor Based on Array of Diffraction Gratings," Sensors and Actuators B, vol. 107, pp. 154-161 (Nov. 2004).

* cited by examiner

*Primary Examiner* — Sang Nguyen (74) *Attorney, Agent, or Firm* — Patrick J. S. Inouye; Krista A. Wittman

(57) ABSTRACT

A surface plasmon resonance coupler and disperser system is provided. A sensor element includes a diffraction grating having a periodically modulated surface. A light source faces the sensor element and emits an optical wave through a collimating element, which is provided in optical alignment with the light source. The optical wave is projected directly onto the periodically modulated surface of the diffraction grating. A detector faces the diffracting grating and is in receipt of the optical wave that is diffracted off the sensor element.

27 Claims, 6 Drawing Sheets

SURFACE PLASMON RESONANCE COUPLER AND DISPERSER SENSOR

CROSS-REFERENCE TO RELATED APPLICATION

This non-provisional patent application claims priority under 35 U.S.C. §119(e) to U.S. Provisional Patent Application Ser. No. 61/052,578, filed May 12, 2008, the disclosure of which is incorporated by reference.

FIELD

The invention relates in general to spectroscopy of surface plasmons, and in particular, to a surface plasmon resonance coupler and disperser, which can be suited for use in detecting biological and chemical events through spectroscopy of surface plasmons.

BACKGROUND

Conventional surface plasmon resonance (SPR) sensors can detect chemical and biological events through spectroscopy of surface plasmons. Surface plasmons are collective oscillations of conduction electrons, which can exist at the physical interface of metal and dielectric media. Surface plasmons can be excited by optical waves. Resonant coupling occurs between the optical wave and the surface plasmons and results in a decrease in intensity of the optical wave. In the attenuated total reflectance method, an optical wave is introduced into an optical prism having a thin metal layer deposited on a base of the prism. When introduced to the base, light evanescently tunnels though the metal film and excites a surface plasmon at the outer boundary of the metal film. Alternatively, an optical wave can be coupled to surface plasmons via diffraction on a meta-coated diffraction grating. When the incident optical wave is polychromatic, the coupling condition is only fulfilled for a narrow band of wavelengths and the spectrum of the optical wave coupled to a surface plasmon contains a characteristic spectral feature, typically a dip. Spectral position of the SPR dip is sensitive to changes in the refractive index of the medium in which the surface plasmon propagates. Therefore, very small changes in the refractive index at the surface of the metal film can be measured by monitoring the position of the SPR dip. The binding of analyte molecules to biorecognition elements immobilized on the surface of the metal film creates a shift in the spectral position of SPR dip-resonant wavelength. The change in the resonance wavelength can be correlated with the concentration of analyte.

SPR sensors are used across many fields. In food quality and safety, SPR sensors have been used to detect bacteria, such as *Escherichia coli* and *Salmonella enteritidis*. SPR sensors can also detect drug residues, hormones, allergens, proteins, chemical contaminants, and toxins produced by bacteria. For medical diagnostics, antibodies, drugs, hormones, and disease biomarkers, including cancer, allergy, and heart attack markers can be identified with SPR to corroborate normal biological and pathogenic processes, or pharmacologic responses to therapeutic intervention. SPR sensors are also used to detect the presence of pesticides and heavy metals in the environment.

Conventional SPR sensors include prism couplers, diffraction gratings, optical fibers, and integrated optical waveguides. These SPR sensors are expensive, large, and often maintained in a centralized laboratory to facilitate sharing. Monitoring immediate changes in environmental or health related conditions are generally impracticable. Moreover, conventional SPR sensors are generally inadequately sized for immediate and mobile use, and cost disfavors widespread adoption.

SUMMARY

A sensitive, compact, flexible, multi-channel surface plasmon resonance (SPR) biosensor is provided for application in the field or home environment. The SPR biosensor is based on a special diffractive structure herein referred to as an SPR coupler and disperser (SPRCD), which excites surface plasmons and simultaneously disperses light, over an image detector. This measurement principle allows the development of a compact and simple instrument with a performance comparable to that of the best spectroscopic. SPR sensors.

A surface plasmon resonance coupler and disperser system is provided. A sensor element includes a diffraction grating having a periodically modulated surface. A light source faces the sensor element and emits an optical wave through a collimating element, which is provided in optical alignment with the light source. The optical wave is projected directly onto the periodically modulated surface of the diffraction grating. A detector faces the diffracting grating and is in receipt of the optical wave that is diffracted off the sensor element.

A further embodiment provides a surface plasmon resonance coupler and disperser system. A sensor element includes a diffraction grating, having a periodically modulated surface. A light source emits a polychromatic optical wave that is projected onto the periodically modulated surface of the diffraction grating. A detector is placed co-planar to the light source and is in receipt of the optical wave, which is diffracted off the sensor element. The sensor element is positioned between the light source and the detector. A mirror includes a concave reflective surface facing each of the light source, sensor element, and detector. The mirror is contoured to reflect the optical wave from the light source onto the periodically modulated surface of the diffraction grating and to further reflect the diffracted optical wave from the diffraction grating onto the sensor.

A further embodiment provides a surface plasmon resonance coupler and disperser system. A sensor element includes a diffraction grating having a periodically modulated surface. A light source emits an optical wave projected onto the periodically modulated surface of the diffraction grating. An imaging element includes a reflective surface. The imaging element is contoured to receive the optical wave that is diffracted off the sensor element and to reflect the incident diffraction of the optical wave. A detector is in receipt of the incident diffraction reflected by the imaging element.

Still other embodiments and applications will become readily apparent to those skilled in the art from the following detailed description, wherein are described embodiments by way of illustrating the best mode contemplated. As will be realized, other and different embodiments are possible and their several details are capable of modifications in various obvious respects, all without departing from the spirit and the scope. Accordingly, the drawings and detailed description are to be regarded as illustrative in nature and not as restrictive.

DETAILED DESCRIPTION

Surface plasmon resonance (SPR) sensors are commonly used to detect and quantify biological and chemical events taking place at the sensor surface, and to identify biological and chemical compounds. Conventional SPR sensors feature complicated optical layouts based on conventional optical components, which are large in size and can be inconvenient to use outside of a laboratory, particularly in a mobile form.

Figure 1:
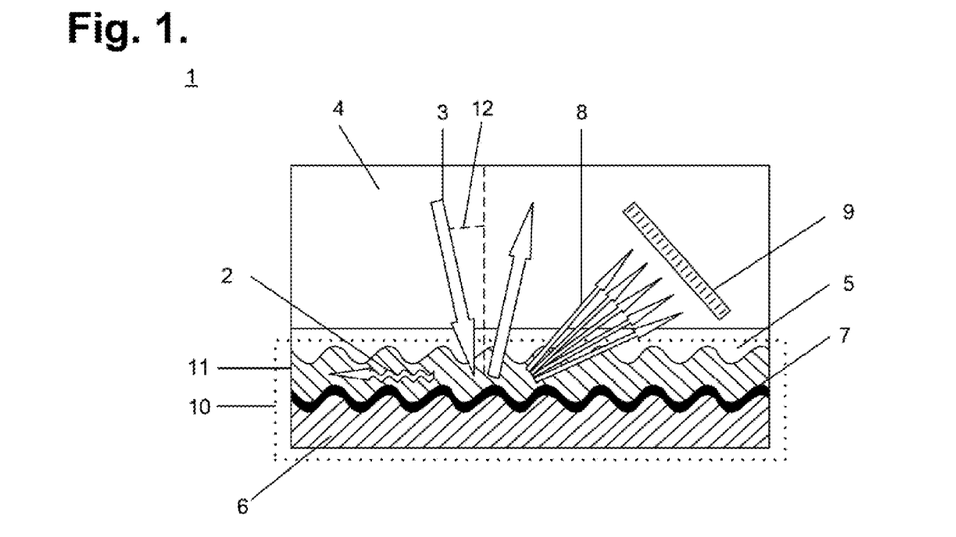
FIG. 1 is a block diagram showing a method of spectroscopy of surface plasmons based on a surface plasmon resonance coupler and disperser.

FIG. 1 is a block diagram illustrating an operating principle of a surface plasmon resonance coupler and disperser (SPRCD) sensor. The operating principle is disclosed in the related, commonly-owned U.S. Pat. No. 7,973,933, issued on Jul. 5, 2011, the disclosure of which is incorporated herein by reference. A sensor element 10 includes a diffraction grating 6, which is covered by a metal layer 7, such as gold or silver. The metal layer 7 of the sensor element 10 can be coated with a layer of biorecognition elements 11. The sensor element 10 and biorecognition elements 11 are in contact with a dielectric medium, which includes a sample to be analyzed 5. An optical wave 3 is projected at an angle of incidence 12 onto the metal layer 7 of the sensor element 10 and excites a surface plasmon 2, which propagates at an interface between the metal layer 7 and the dielectric medium 5. As a result of the coupling, the optical wave 3 transfers a part of its energy at a resonant wavelength to the surface plasmon 2. Upon receipt of the optical wave 3 on the sensor element 10, the optical wave 3 is diffracted 8. A detector 9 measures spatial distribution of the intensity of the diffracted optical wave 8. The spatial distribution of intensity is associated with the wavelength spectrum of the optical wave, which is coupled to a surface plasmon during surface plasmon resonance. The surface plasmon resonance results in a dip in the wavelength spectrum, and the intensity of the optical wave decreases to a minimum intensity at the resonant wavelength.

To quantify biological and chemical events or to identify a compound, a sample with a particular analyte is brought into contact with the biorecognition elements 11 on the metal layer 7, and the analyte can bind to the biorecognition elements. The biorecognition elements 11 are selected by their affinity for binding with a particular analyte. The analyte can be identified based on the specific biorecognition binding, which produces a shill of the resonant wavelength measured by the detector 9. A sensorgram (not shown) records a change in the resonant wavelength in the spectrum of the diffracted optical wave. A shift of the resonant wavelength is proportional to the amount of the bound analyte. The sensorgram provides a record of the binding characteristics, including association and dissociation of the analyte with the immobilized biorecognition elements 11.

SPRCD Sensor Based on Far-Field Projection

Figure 2:
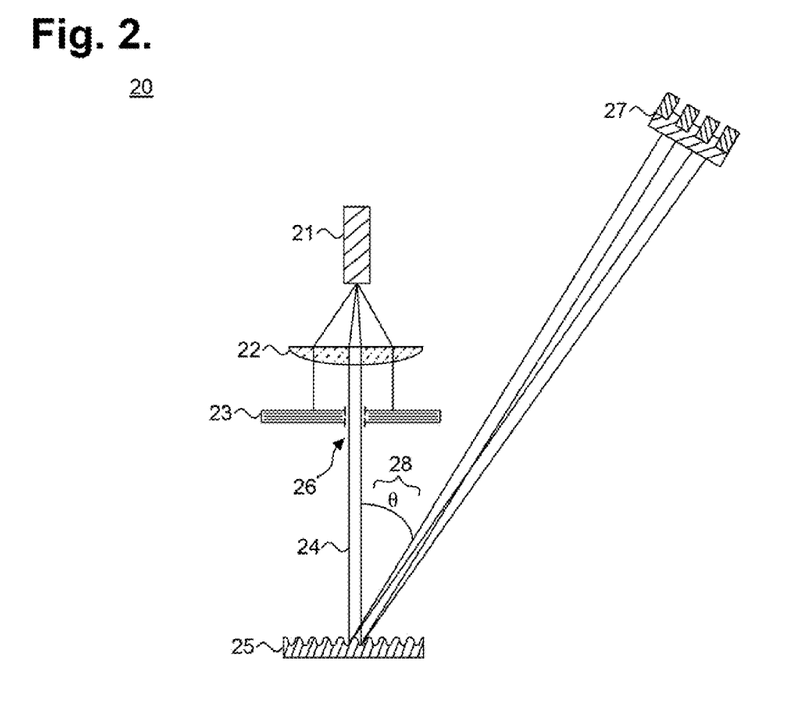
FIG. 2 is a block diagram showing an optical system for a surface plasmon resonance coupler and disperser sensor based on far field projection.

A far field lens-based surface plasmon resonance coupler and disperser (SPRCD) sensor overcomes existing size and cost concerns by minimizing the number of optical components utilized. FIG. 2 is a block diagram showing an optical system 20 for an SPRCD sensor based on far-field projection. The SPRCD sensor includes a light source 21, which emits an optical wave 24 with a finite wavelength spectrum through a collimating element 22 along an incident path. The collimating element can include a parabolic mirror, spherical mirror, toroidal mirror, spherical lens, and aspheric lens. Other collimating elements are possible. As used herein, any reference to an "optical wave," "electromagnetic wave," "light wave," or "light" will be understood to include the other term, except as specifically indicated otherwise. The optical wave 24 can include polychromatic light. The light source 21 can include light emitting diodes ("LEDs"), filament lamps, discharge lamps, or super luminescent diodes. Other light sources are possible.

The collimating element 22 collimates the optical wave 24 to generate a parallel beam of light. The collimating element 22 can include a molded acrylic aspheric lens or other type of lens. The focal length of the collimating element is selected based on the properties of the optical wave emitted by the light source to achieve the required incident light beam with a divergence or convergence of less than 0.3 degrees. For example, the optimum focal length of about 12-15 mm is used for a point source LED with 50 μm spot. In a further embodiment, the light source 21 and the collimating element 22 can be integrated into a single housing (not shown) to produce a robust and stable source of a continuous collimated optical wave 24 having a divergence of less than 0.3 degrees. The housing can be made from aluminum or other types of material. The optical wave 24 is projected along the incident path through an aperture 26 in a lens diaphragm 23 and made incident onto a sensor element 25. The lens diaphragm can include one of a circular or rectangular shape. The aperture 26 controls the optical wave 24 by restricting and admitting light passed through the collimating element 22 and confines the optical wave 24 to a specific area on the sensor element 25. The size of the aperture 26 depends on the divergence of the incident optical wave 24, in one embodiment, the width of the aperture is less than 1 mm. Other widths are possible. In a further embodiment, the lens diaphragm 23 is optional. When not included, the optical wave 24 is projected directly from the light source 21 through the collimating element 22 and onto the sensor element 25.

The sensor element 25 includes a diffraction grating having a periodically modulated surface, which is covered with a metal layer, such as gold or silver. Other types of metals are possible. The periodically modulated surface can include different configurations, such as uniform sinusoids. A pitch and a depth are associated with the sinusoidal surface, which when varied, affect a value of the resonant wavelength and a width of the SPR dip. Other configurations and grating surfaces are possible.

The light source 21, collimating element 22, lens diaphragm 23, and sensor element 25 are each located along the incident path. The length of the incident path is determined by the properties and sizes of the used components, and can be between 20 mm and 300 mm. The light source 21 is located at a base of the incident path and the sensor element 25 is located opposite the light source 21, at an apex of the incident path. The distance between the light source 21 and the sensor element 25 can be adjusted without significant effect on the performance of the SPRCD sensor based on far-field projection. The collimating element 22 and the lens diaphragm 23 are aligned along the incident path between the light source 21 and the sensor element 25. The collimating element 22 can include the lens diaphragm 23 or alternatively, the collimating element 22 and the lens diaphragm can be implemented as separate elements. When implemented separately, the collimating element 22 is located along the incident path after the light source 21. The lens diaphragm 23 is then located along the incident path after the collimating element 22 and before the sensor element 25. In a further embodiment, the light source 21 can include the collimating element 22 and the lens diaphragm 23.

Upon introduction onto the sensor element 25, the incident electromagnetic wave 24 is diffracted along a detection path located at an angle 28 from the incident path. The angle 28 between the incident path and the detection path is determined by the pitch of the diffraction grating and the wavelength of the incident optical wave 24 on the diffraction grating. For example, for a wavelength of 850 nm and a grating pitch of 1250 nm, the angle is about 42.8 degrees. Other methods for determining the angle are possible. The detector 27 is located at an apex of the detection path opposite the sensor element 25, which is located at a base. The detector 27 records the spatial distribution of light across the diffracted optical wave 24. The size of the detector 27 can be determined by the size of the aperture 26 in the lens diaphragm 23. The distance between the detector 27 and the sensor element 25 can be varied to adjust the wavelength resolution for optimal performance of the SPRCD sensor based on far-field projection. The distance depends on one or more of the size of the aperture 26, the diffraction grating pitch, the divergence of the incident optical wave 24, the utilized wavelength spectrum of the optical wave, the shape of the SPR resonance, and the size of the detector 27. In one embodiment, a distance of about 200 mm, absent other considerations, requires an aperture size of 1 mm, divergence of 0.3 degrees, a utilized wavelength spectrum of 830 nm-860 nm, normal incidence of optical wave on the grating, a grating pitch of 1250 nm, and a detector size to fit an image having the dimensions 9 mm×6.7 mm. Other distances and methods for calculating the distances are possible.

During diffraction, the wavelength spectrum of the incident optical wave 24 is dispersed into an angular spectrum in which each wavelength corresponds to a different angle of diffraction. The detector 27 records a spatial distribution of light intensity, which is used to determine the angular spectrum of the dispersed optical wave 24. Once determined, the spatial distribution of light intensity can be analyzed to determine a resonant wavelength at which surface plasmon resonance occurs. The spectrum of the optical wave 24 coupled to a surface plasmon contains a characteristic spectral feature, typically a dip. The detector 27 can include a charge-coupled device (CCD), photo-diode array (PDA), or complementary metal-oxide semiconductor detector (CMOS). Other detectors are possible.

Performance of the SPRCD sensor with far-field projection 20 can be altered by adjusting a length of the detection path, that is, the distance between the sensor element 25 and the detector 27. An optimal distance between the sensor element 25 and the detector 27 can be determined from the wavelength resolution required for resolving the position of the SPR dip. The wavelength resolution can be theoretically analyzed by ray-trace of the optical layout considering the angular separation of the diffracted wavelength components, a utilized wavelength spectrum, a diameter of the incident electromagnetic wave 24, and the diffraction of the electromagnetic wave 24 on the aperture 26.

The optical components can be fixed to an optical bench made from metal or plastic material. Other types of material are possible. The optical bench can include a layer of material upon which the optical components are affixed. Alternatively, the optical components, including the light source 21, collimating element 22, lens diaphragm 23, sensor element 25, and detector 27 can be arranged in a housing to generate the SPRCD sensor with far-field projection for convenient and portable use. The housing conformably surrounds the optical components and can be made from heavy plastic material, such as epoxy. The housing can include multiple sides. However, at a minimum, the housing must include three sides for supporting the light source 21, sensor element 25, and detector 27.

Within the housing, the light source 21 is located on a light generating side of the housing, whereas, the sensor element 25 is located opposite the light source 21, on a diffraction side of the housing. The collimating element 22 and lens diaphragm 23 are interspersed between the light source 21 and sensor element 25. In one embodiment, the collimating element 22 is placed after the light source 21 and the lens diaphragm 23 is placed after the collimating element 22 and before the sensor element 25. The detector 27 is located at an angle from the sensor element 25 on a detection side of the housing. The angle is determined by the grating, pitch, the wavelength of optical wave, and the laws of optical diffraction. For example, a wavelength of 850 nm, normal incidence of optical wave on the grating and a grating pitch of 1250 nm yield the angle of diffraction of 42.8 degrees with respect to the incident optical wave 24.

Figure 3:
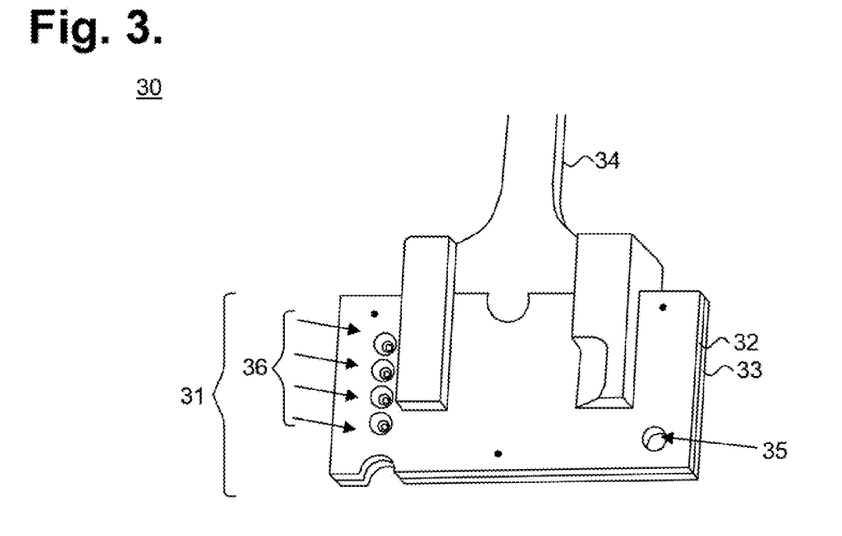
FIG. 3 is a block diagram showing, by way of example, a surface plasmon resonance coupler and disperser cartridge and cartridge holder.

The housing can also be configured to affix the sensor element to the diffraction side of the housing or to receive a removable SPRCD cartridge, which includes an optical window cover and the sensor element 25 via a cartridge slot. The cartridge slot is formed within the diffraction side of the housing or alternatively, within a sample side of the housing that interconnects the light generating, diffraction, and detection sides of the housing, as well as any other sides by enclosing the optical components and serves as a top side of the housing. FIG. 3 is a block diagram showing, by way of example, an SPRCD cartridge 31 and cartridge holder 34. The SPRCD cartridge 31 includes art optical window cover 33 and a sensor element 32, which can be covered with a metal layer and a layer of biorecognition elements. The biorecognition elements can be directly attached to the metal layer or can be immobilized through one or more linker layers. The optical window cover 33 can be made of glass or transparent plastic material, such as CR39 plastic; however, other materials are possible. One or more microfluidic channels can be formed on or in the optical window cover 32 or sensor element 33. For each microfluidic channel formed, an input port 36 is formed within the optical window cover 32 or sensor element 33. Each input port includes an opening configured to receive a sample tube. The optical window 32 or the sensor element 33 can also include a common output port 35 for all the channels, which includes a single opening to receive a waste tube. In a further embodiment, each microfluidic channel can be associated with a separate waste tube. The sample tubes and the output tubes are affixed to the housing of the SPRCD sensor and can be respectively configured to receive and distribute samples, which include analyte.

The microfluidic channels can be formed directly in the optical window cover 32, directly in the sensor element 33, or can be produced by affixing shaped gaskets, laser-etched foil or mechanically cut channels between the sensor element 33 and the optical window cover 32. The gaskets can be formed from polyester or vinyl and the foil layer can include a self-adhesive layer. Other gaskets and foils could be used.

The optical window cover 32 is placed on top of the sensor element with the microfluidic channels positioned between the sensor element 33 and the optical window cover 32. Once formed, the SPRCD cartridge 31 can be inserted into the SPRCD sensor via the cartridge holder 34. The cartridge holder 34 is configured to receive the SPRCD cartridge 31 for easy insertion and removal from the housing of the SPRCD sensor, as well, as for easy storage of the SPRCD cartridge 31 while not in use. The cartridge holder 34 can be affixed to the housing of the SPRCD sensor or alternatively, the cartridge holder 34 can be attached to the SPRCD cartridge 31. The cartridge holder 34 can be made from plastic and can be disposable; however, other types and positions of cartridge holders 34 are possible. When the SPRCD cartridge 31 is positioned within the SPRCD sensor, the sample tubes and waste tubes are respectively inserted and sealed into the input and output ports in the SPRCD cartridge 31. A user can apply a sample to each input tube, which flows through the respective microfluidic channel and out through the waste tube. The SPRCD sensor based on far-field projection continuously collects spectra of the diffracted optical wave from the individual microfluidic channels and calculates the resonant wavelengths, which produce a sensor response from all channels in real time. In a further embodiment, the housing can include a USE port for transmitting the collected data, which is translated into an electric signal for transferring to a USB host.

Mirror-Based SPRCD Sensor

Figure 4:
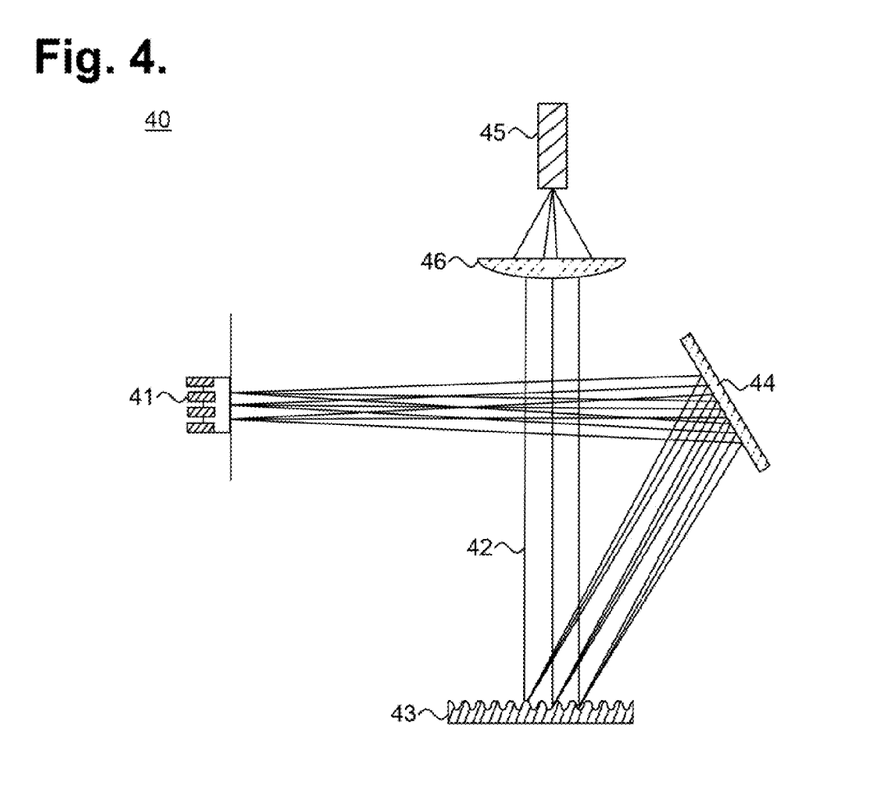
FIG. 4 is a block diagram showing an optical system for a mirror-based surface plasmon resonance coupler and disperser sensor.

A mirror-based SPRCD sensor addresses concerns regarding size, wavelength resolution, and light throughput by including additional imaging components to reduce the diffraction path. A toroidal mirror enables utilization of a larger diameter of an incident optical wave and thus, improves the light throughput and signal to noise ratio of a measured signal. FIG. 4 is a block diagram showing an optical system 40 for a mirror-based surface plasmon resonance coupler and disperser sensor. The mirror-based SPRCD sensor includes a light source 45, which emits an optical wave 42 with a finite wavelength spectrum through a collimating element 46 along an incident path. The light source 45 can include LEDs, filament lamps, discharge lamps, or super luminescent diodes. The optical wave 42 can include polychromatic light. Other types of light and light sources are possible.

The collimating element 46 collimates the optical wave 42 to generate a parallel beam of light. The collimating element 46 can include a parabolic mirror, spherical mirror, toroidal mirror, spherical lens, and aspheric lens, as well as other collimating elements. The focal length of the collimating element 46 is selected based on the type of light source needed to achieve a collimated beam divergence of less then 0.3 degrees. Other beam divergence values are possible. For a point source LED with a 50 µm spot, a focal length of 12 mm can be used. Other focal lengths and methods for determining focal lengths are possible. In a further embodiment, the light source 45 and the collimating element 46 can be integrated into a single housing to produce a robust and stable source of a continuous collimated beam of light with a divergence of less than 0.3 degrees. The light source 45 and collimating element 46 housing can be made from aluminum or other types of material.

The optical wave 42 is made incident onto a sensor element 43, which is located at an apex of the incident path. The sensor element 43 can include a diffraction grating having a periodically modulated surface that can be covered with a metal layer, including gold or silver, and a layer of biorecognition elements. Other types of metal are possible. The biorecognition elements can be directly attached to the metal layer or can be immobilized through one or more linker layers. The periodically modulated surface can include different configurations, such as uniform sinusoids. Other configurations and grating surfaces are possible. Achieving optimum performance can be based on varying the profile of the grating and the utilized wavelength. For example, a pitch and to depth of the sinusoidal surface of the grating can affect a value of the resonant wavelength and a width of the SPR dip.

The incident optical wave 42 is diffracted and the wavelength spectrum is dispersed upon introduction to the sensor element 43. The incident optical wave 42 is diffracted in the direction of a diffraction path. The angle between the incident path and the diffraction path can be determined by the pitch of the diffraction grating and the utilized wavelength of the incident light wave. For example, an angle of 42.8 degrees is formed from a wavelength of 850 nm and a grating pitch of 1250 nm. Once diffracted, the incident optical wave 42 is received by a mirror 44 along the diffraction path and then reflected onto a detector 41 along a detection path. The mirror 44 is located at an apex of the diffraction path while the sensor element 43 is located at a base. The mirror 44 can include a toroidal mirror, as well as other types of mirrors. The detector 41 is located in a back focal plane of the mirror 44 in such a way, that a parallel beam received along the detection path is focused on the detector 41 in the plane defined, by the incident path and the diffraction path.

The mirror 44 can be designed with a different radius of curvature in different planes. The radii of curvature of the mirror 44 can determine the size and position of the detector 41, including the distance of the detector 41 from the mirror. In one embodiment, the different radii of mirror curvature can be 50 mm and 150 mm, while the distance between the mirror and detector can be 74 mm. The back focal plane of the mirror 44 in the plane defined by the incident path and the detection path is located on the detector surface, and the surface of the sensor element is imaged on the detector surface in the perpendicular plane. In a further embodiment, lenses can be incorporated to replace the mirror. The position of the mirror 44 is adjustable to compensate for variation in the manufacturing process of the mirror-based SPRCD sensor.

Figure 5:
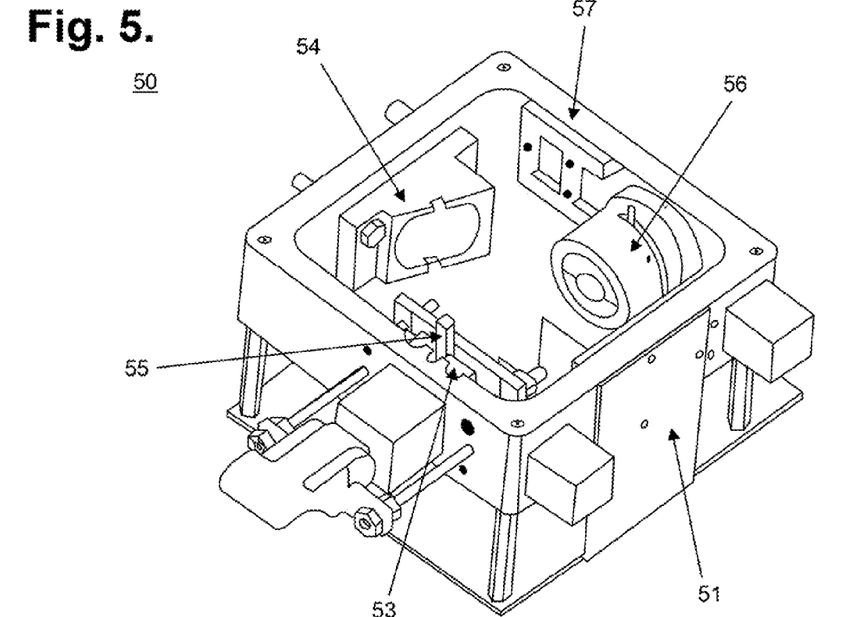
FIG. 5 is a block diagram showing, by way of example, a cross-section of a mirror-based surface plasmon resonance coupler and disperser sensor.

The detector 41 is located across from the minor 44 at an apex of the detection path. The detection path is perpendicular to the incident path. Different directions of the detection paths are possible based on the design and orientation of the mirror 44. The detector 41 records the spatial distribution of light intensity of the diffracted optical wave 42, which is used to determine an angular spectrum of dispersed light and consequently the wavelength spectrum of the diffracted optical wave 42. The detector 41 can include a CCD, PDA, or CMOS detector. Other detectors could be used. The optical components of the mirror-based SPRCD sensor can be located in a housing for portable and convenient use. FIG. 5 is a block diagram showing, by way of example, a cross-section of a mirror-based SPRCD sensor 50. A housing 57 conformably surrounds the optical system components of the mirror-based SPRCD sensor 50, including the light source 56, sensor element 53, mirror 54, and detector 51. At a minimum the housing should include four sides, one for each of the light source 56, sensor element 53, mirror 54, and detector 51. Together, the four sides can form a square or rectangle. However, more than four sides can be used to change the size and shape of the mirror-based SPRCD sensor 50. The minor-based SPRCD sensor 50 can include dimensions less than 90 mm×90 mm×60 mm. The housing 57 can be made from heavy plastic, such as epoxy. The optical components can also be fixed to an optical bench made of metal or plastic material. The optical bench can include a substantially flat layer of the material upon which the optical components are affixed. Other types of material could be used.

The light source 56 is located within the housing 57 on a light generating side. The sensor element 53 is located on a diffraction side of the housing 57, which is opposite to the light generating side. The mirror 54 is located on a reflection side of the housing 57, which is placed between the light generating side and the diffraction side. The reflection side of the housing can be positioned perpendicular to the light generating and diffraction sides. Alternatively, the reflection side can be positioned at a diffraction angle from the incident path, which is further discussed below with reference to FIG. 6. The diffraction angle is determined by the SPRCD grating pitch, the wavelength of optical wave, and the laws of diffraction. The mirror 54 can be adjusted within the housing 57 to compensate for variation in manufacturing of the mirror-based SPRCD sensor 50. The detector 51 is located on a detection side of the housing, across from the reflection side and between the light generating side and the diffraction side. Other positions of the detector can be used in combination with different mirrors. Top and bottom sides can interconnect the light generating, diffraction, reflection, and detection sides by enclosing an area formed by those sides.

Figure 6:
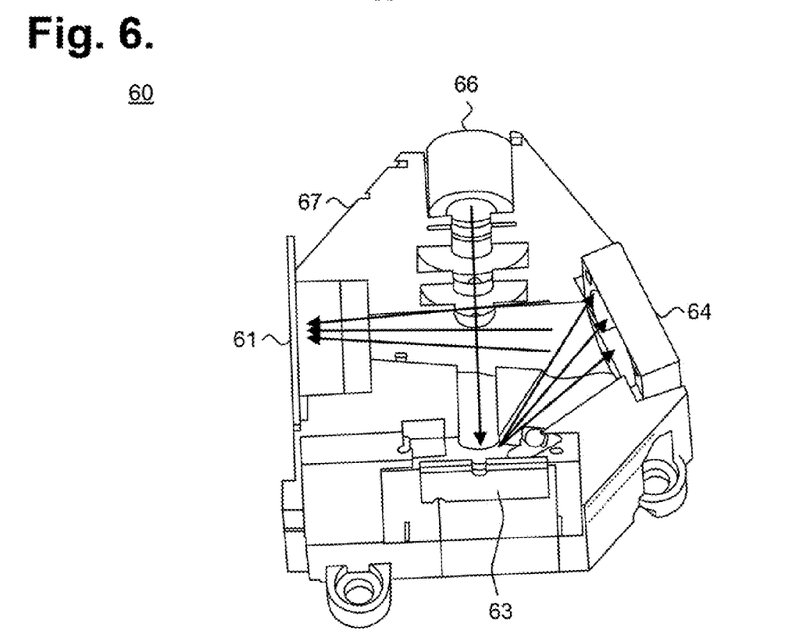
FIG. 6 is block diagram showing, by way of example, a further embodiment of a cross section of the surface plasmon resonance coupler and disperser sensor of FIG. 5.

In a further embodiment, the housing for the mirror-based SPRCD sensor can include more than four sides. FIG. 6 is block diagram showing, by way of example, a further embodiment of a cross-section of the mirror-based surface plasmon resonance coupler and disperser sensor 60 of FIG. 5. The further embodiment of the mirror-based SPRCD sensor 60 contains optical components, including a light source 66, sensor element or SPRCD cartridge 63, mirror 64, and detector 61. The optical components can be positioned within a housing 67. The light source 66 is located within the housing 67 on a light generating side. The sensor element 63 is located on a diffraction side, which is opposite to the light generating side. The mirror 64 is located on a reflection side of the housing 67, which is placed at an angle between the light generating side and the diffraction side. The angle can be determined by a grating pitch of the sensor element 63, the wavelength of the optical wave, and the laws of diffraction. Further one or more sides can be implemented between the reflection side and the light generating or diffraction sides. The detector is located on a detection side of the housing across from the reflection side and in between the light generating and diffraction sides. One or more sides can be positioned between the detection side and the light generating and diffraction sides. Changing the number and sizes of the sides can vary the shape and size of the sensor. Top and bottom sides can be placed to fully enclose the optical components.

Regardless of the number of sides included in the housing, the housing 57 can include a cartridge slot configured to receive a cartridge holder 55 and an SPRCD cartridge 53, which can be used in place of the sensor element 53. The cartridge slot can be located within the diffraction, top, or bottom sides of the housing 57, as well as other sides. The SPRCD cartridge 53 can include the sensor element 53, which is covered by an optic window cover. The optic window cover can be made from glass or transparent plastic, such as CR39 plastic; however, other types of plastic and material are possible. One or more microfluidic channels can be formed directly in the optical window cover, directly in the sensor element 53, or can be produced by affixing shaped gaskets, laser-etched foil or mechanically cut channels between the sensor element 53 and the optical window cover. The gaskets can be formed from polyester or vinyl and the foil layer can include a self-adhesive layer. Other gaskets and foils could be used. For each microfluidic channel, an input port, which includes an opening configured to receive a sample tube, can be formed in the optical window cover or sensor element 53 of the cartridge. The optical window cover or the sensor element 53 can also include a common output port for all the microfluidic channels, which includes an opening to receive a waste tube. Alternatively, each microfluidic channel can include a separate output port. The sample tubes and the output tubes are affixed to the housing 57 of the SPRCD sensor 50.

The cartridge holder 55 can be made from plastic and can be permanently or removably affixed to the housing 57. The cartridge holder 55 can include two C-shaped brackets affixed to a cross bar and configured to receive the SPRCD cartridge. The cross bar is further affixed perpendicularly to a longitudinal bar that is used to maneuver the SPRCD cartridge 53 in and out of the mirror-based SPRCD sensor. During insertion into the housing, the cartridge holder 55 guides the SPRCD cartridge 53 into the cartridge slot located on one of the diffraction, top, or bottom sides of the housing. The SPRCD cartridge 53 is aligned in the cartridge slot by, for example, aligning pins affixed to the housing and a complementary opening in the SPRCD cartridge. Other methods for alignment are possible. Once the SPRCD cartridge is aligned, the sample tubes are properly inserted into the input ports and the waste tube is inserted into the output port.

Figure 7:
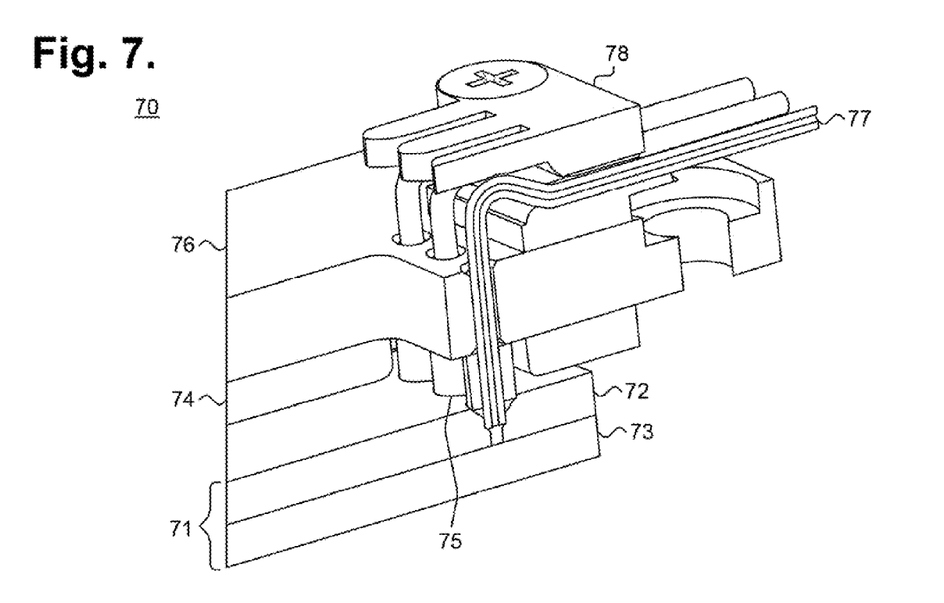
FIG. 7 is a block diagram showing, by way of example, a cartridge inserted in a surface plasmon resonance coupler and disperser sensor and interfaced with a fluidic system of the sensor.

FIG. 7 is a block diagram 70 showing, by way of example, a cross-section of an SPRCD cartridge 71 inserted in a surface plasmon resonance coupler and disperser sensor and interfaced with fluidic system of the sensor. The SPRCD cartridge 71 is inserted into a cartridge slot within the housing of the SPRCD sensor. The SPRCD cartridge 71 includes a sensor element 73 covered by a metal layer and an optical window cover 72 with one or more microfluidic channels 77 formed between the sensor element 73 and optical window cover 72. A rubber layer 74 can be placed upon the optical window cover 72 and can include openings configured to receive sample tubes 77 and output tubes 77. A pressure distributing material 76 can be positioned upon the rubber layer 74 to apply a constant and evenly distributed pressure for preventing the leaking of a sample introduced to the SPRCD cartridge 71 via the sample and waste tubes 77. The pressure distributing material 76 can include openings configured to receive sample tubes 77 and output tubes 77 that are consistent with the openings of the rubber layer 74. The sample and waste tubes 77 are placed into the openings and secured to the SPRCD cartridge by a sealing O-ring 75 placed around each tube. The sealing O-ring 75 can be a part of the rubber layer 74 or separate. More specifically, the sample tubes 77 and waste tubes 77 are affixed to the housing and originate along a top surface of the pressure distributing metal layer 76 and then down through the pressure distributing metal layer 76 and the rubber layer 74 to be received by an input port formed in the optic window cover 72. The waste tube 77 originates at an output port formed in the optic window cover 72 and extends up through the rubber layer 74 and pressure distributing metal layer 76, out of which the waste tube exits 77. The tubes 77 are affixed to the pressure distributing metal layer 76 using a tube holder 78 or ferula sticking, into the cartridge reception slot in such a way, that it connects and seals with the input and output ports of the SPRCD cartridge 71 when inserted into the housing. In a further embodiment, the input and output ports can be formed in the sensor element. Other means for securing the sample and waste tubes are possible.

Once the SPRCD cartridge 71 is in place, a user can apply a sample containing a specific analyte to each sample tube 77. The sample flows through the sample tube to the respective microfluidic channel. Biorecognition elements, which have a specific binding affinity for a particular analyte, can be immobilized on the metal layer of the sensor element. As the sample passes through the microfluidic channel and over the sensor element, the analyte can bind to the immobilized biorecognition elements. The sample travels through the microfluidic channel to the output port and through the waste tube. The measured sample is delivered to the sensor element via the input tubes using a peristaltic pump. Other pumps and liquid delivery systems are possible. The mirror-based SPRCD sensor continuously collects spectra of the diffracted optical wave from the individual microfluidic channels and calculates the resonant wavelengths, which produces a sensor response from all channels in real time. The housing of the SPRCD sensor can incorporate a USB port for transmitting the collected data to a computer.

Figure 8:
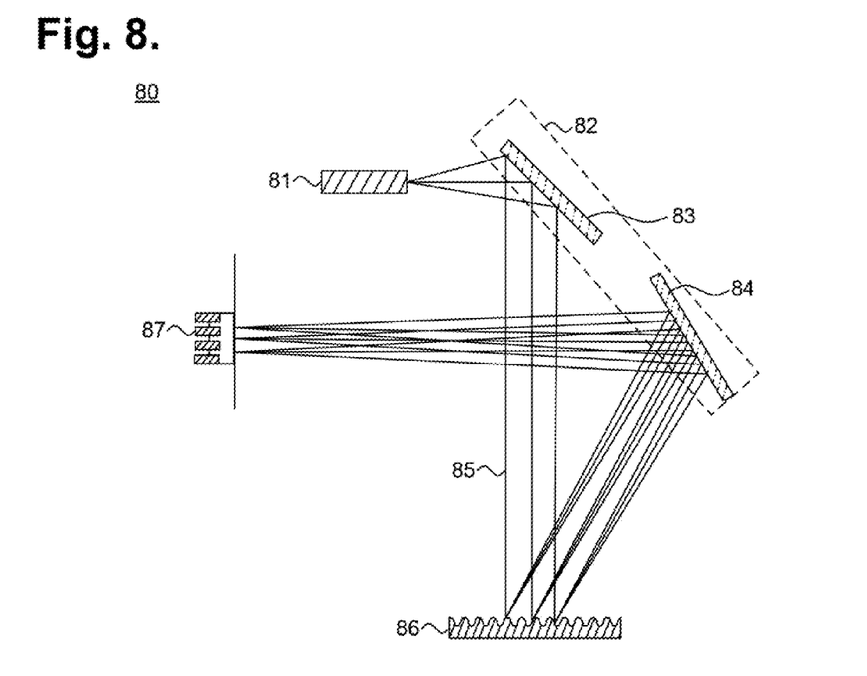
FIG. 8 is a block diagram showing an optical system for a further embodiment of the mirror-based surface plasmon resonance coupler and disperser sensor of FIG. 4.

In an alternative embodiment, the size of the mirror-based SPRCD sensor can be further reduced by adding an additional mirror. FIG. 8 is a block diagram showing an optical system 80 for a further embodiment of the mirror-based surface plasmon resonance coupler and disperser sensor of FIG. 4. A light source 81 emits an optical wave 85 having a finite wavelength spectrum along a collimating path onto a collimating element, such as a first mirror 83, which collimates the optical wave 85 to generate a beam of collimated light. The collimating element can also include a parabolic minor, spherical mirror, toroidal mirror, spherical lens, and aspheric lens. Other mirrors and lenses are possible. The optical wave 85 can include polychromatic light. The focal length of the mirror 83 is selected based on the type of the light source required to achieve a collimated beam of light having a divergence of less than 0.3 degrees. Other beam divergences are possible. The light source 81 is located at a base of the collimating path and the first mirror 83 is located at an apex. The light source 81 can include light emitting, diodes, filament lamps, discharge lamps, or super luminescent diodes. Other types of light sources are possible.

The optical wave 85 is reflected off the first mirror 83 along an incident path and made incident onto a sensor element 86. The first mirror 83 is located at a base of the incident path and the sensor element 86 is located at an apex. The sensor element 86 can include a diffraction grating having a periodically modulated surface covered with a metal layer, such as gold or silver, and a layer of biorecognition elements. Other types of metals could be used. The biorecognition elements can be directly attached to the metal layer or can be immobilized through one or more linker layers. The periodically modulated surface can include different configurations, such as sinusoids. Other configurations and grating surfaces are possible. The sinusoidal surface is associated with a pitch and depth of the sinusoids, which can vary. Variations of the pitch and depth of the sinusoids affect the excitation of surface plasmons. For example, an increase in the period of a sinusoidal grating of 10 nm creates an increase in the resonant wavelength of about 6.3 nm. Other variations and effects are possible.

The incident optical wave 85 is diffracted and the wavelength spectrum is dispersed upon introduction to the sensor element 86. The incident optical wave 85 is diffracted at an angle in the direction of a diffraction path. The angle between the incident path and the detection path is determined by the pitch of the SPRCD grating and the utilized wavelength of the incident optical wave. For example, a wavelength of 850 nm and a grating pitch of 1250 nm forms an angle of about 42.8 degrees. Other methods and factors for use in determining the angle are possible. Once diffracted, the incident optical wave 85 is received by an imaging element, such as a second mirror 84 located at an apex of the diffraction path and reflected onto a detector 87 located at an apex of a detection path. The imaging element can also include at least one of a toroidal mirror, spherical mirror, parabolic mirror, lens, and lens assembly. The sensor element 86 is located at a base of the diffraction path, while the second mirror is located at a base of the detection path. The second mirror 84 can include a toroidal mirror, a parabolic mirror, or other type of mirror. The collimating and imaging elements can be positioned separately or included on a single optic board. More specifically, the first and second mirrors can be of the same mirror or different. If different, the first and second mirrors can be included on a single optical bench 82. Alternatively, the first mirror 83 and the second mirror 84 can be implemented separately. In one embodiment, the first mirror is a parabolic mirror and the second mirror is a toroidal mirror.

The second mirror 84 reflects the diffracted optical wave 85 onto the detector 87, which collects data from the dispersed wavelength spectrum of the diffracted optical wave to measure changes in intensity due to surface plasmon resonance. The detector 87 records the spatial distribution of light intensity, which is used to determine an angular spectrum of the dispersed light and consequently the wavelength spectrum of the diffracted optical wave. The detector 87 can include a CCD, PDA, or CMOS detector. Other types of detectors are possible.

The optical components can be affixed to an optical bench made of metal or plastic material. The optical bench can include a substantially flat layer of the material upon which the optical components are affixed. Alternatively, the components can be enclosed by a housing made from a material, such as epoxy. Other materials are possible. The light source can be located on an electronic side of the housing. In a further embodiment, the light source and the detector and can be mounted on the electronics side on a single circuitry board. The first 83 and second 84 mirrors are located proximate to each other on a mirror side of the housing, which is located at an angle opposite the electronics side. The mirrors 83, 84 can be combined into a single optical reflecting component or can be affixed on a same optical bench. The first mirror 83 is affixed to the optical bench at a specified angle to produce a collimated beam of the optical wave 85. In one embodiment the angle at which the first mirror 83 reflects a central ray of the incident optical wave can be 45 degrees, which allows for easier arrangement of individual optic, electronic, and fluidic components within the housing. Other angles are possible. The sensor element 86 is located on a diffraction side of the housing, which is located between the electronic and mirror sides of the housing. The diffraction side is positioned at a normal angle with respect to the incident optical wave. Other angles are possible. Achieving optimum performance can be based on varying the surface of the grating and the wavelength of the optical wave. The SPRCD detector 87 is located on a detection side between the light generating side and the diffraction side. Alternatively, the detector 87 can be located on the light generating side next to the light source 81 and nearest to the diffraction side. At a minimum the housing should include at least three sides, one for the light source 81 and detector 87, the second for the sensor element 86, and the third for the first 83 and second 84 mirrors. However, more than three sides are possible to form different sizes and shapes of the alternate mirror-based SPRCD sensor.

The housing of the alternate mirror-based sensor can also be configured to removably receive an SPRCD cartridge as described above with respect to the minor-based SPRCD sensor. Input and output tubes can be affixed to the housing to provide a sample to and collect the sample from the SPRCD cartridge, as described above with respect to the minor-based sensor. The alternative mirror-based. SPRCD sensor continuously collects spectra of the diffracted optical wave from the individual microfluidic channels and calculates the resonant wavelengths, which produce a sensor response from all channels in real time. In a further embodiment, the housing can include a USB port for transmitting the collected data, which is translated into an electric signal for transferring to a USB host.

Parallel SPRCD Sensor

Figure 9:
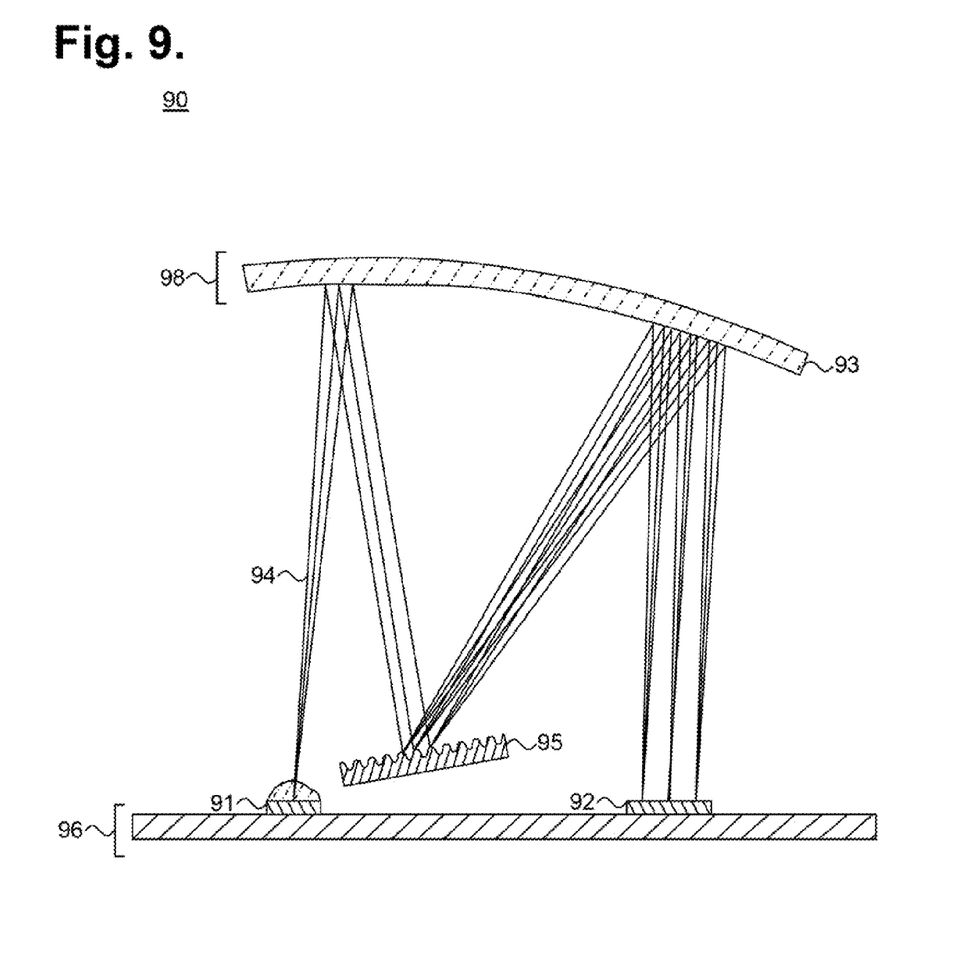
FIG. 9 is a block diagram showing an optical system for a parallel surface plasmon resonance coupler and disperser sensor.

FIG. 9 is a block diagram showing an optical system 90 for a parallel surface plasmon resonance coupler and disperser sensor. The parallel SPRCD sensor includes a sensor board 96 and an optical board 98. The sensor hoard 96 can include a light source 91, a detector 92 positioned co-planar to the light source 91, and the electronics circuitry, while the optical board 98 can include a spherical mirror 93. Other mirrors are possible. The light source 91 emits an optical wave 94 associated with a wavelength spectrum onto the mirror 93. The light source 91 can include light emitting diodes, filament lamps, discharge lamps, or super luminescent diodes. The optical wave 94 can include polychromatic light. Other types of light and light sources are possible.

Upon reflection, the mirror 93 collimates the optical wave 94 to generate a beam of collimated light, which is projected onto a sensor element 95. The electromagnetic wave 94 is diffracted and the associated wavelength spectrum is dispersed onto the mirror 93. The sensor element 95 is removably located between the light source 91 and the detector 92 and can be affixed to the sensor board 96 or located in between the sensor board 96 and the optical board 98. The sensor element 95 can include a diffraction grating having a periodically modulated surface covered by a metal layer, such as gold or silver, and a layer of biorecognition elements. Other types of metals are possible. The biorecognition elements can be directly attached to the metal layer or can be immobilized through one or more linker layers. The periodically modulated surface can include, many configurations, such as sinusoids. Other configurations and grating surfaces are possible.

Once received, the mirror 93 reflects the diffracted optical wave 94 onto a detector 92, which is located approximately in the back focal plane of the mirror 93. Therefore, a parallel beam of the optical wave 94 received from the sensor element 95 is focused on the detector 92. The mirror 93 can include a single spherical mirror, which is used to image the incident optical wave 94 along the detection path. However, a set of two or more mirrors, including spherical mirrors, toroidal mirrors, other mirrors or as combination of the mirrors are possible. The detector 92 records a spatial distribution of light intensity across the beam of the diffracted electromagnetic wave 94. The recorded spatial distribution is used to determine an angular spectrum of the dispersed light and consequently the wavelength spectrum of the diffracted optical wave. The detector 92 can include a CCD, PDA, or CMOS detector. Other detectors are possible.

Figure 10:
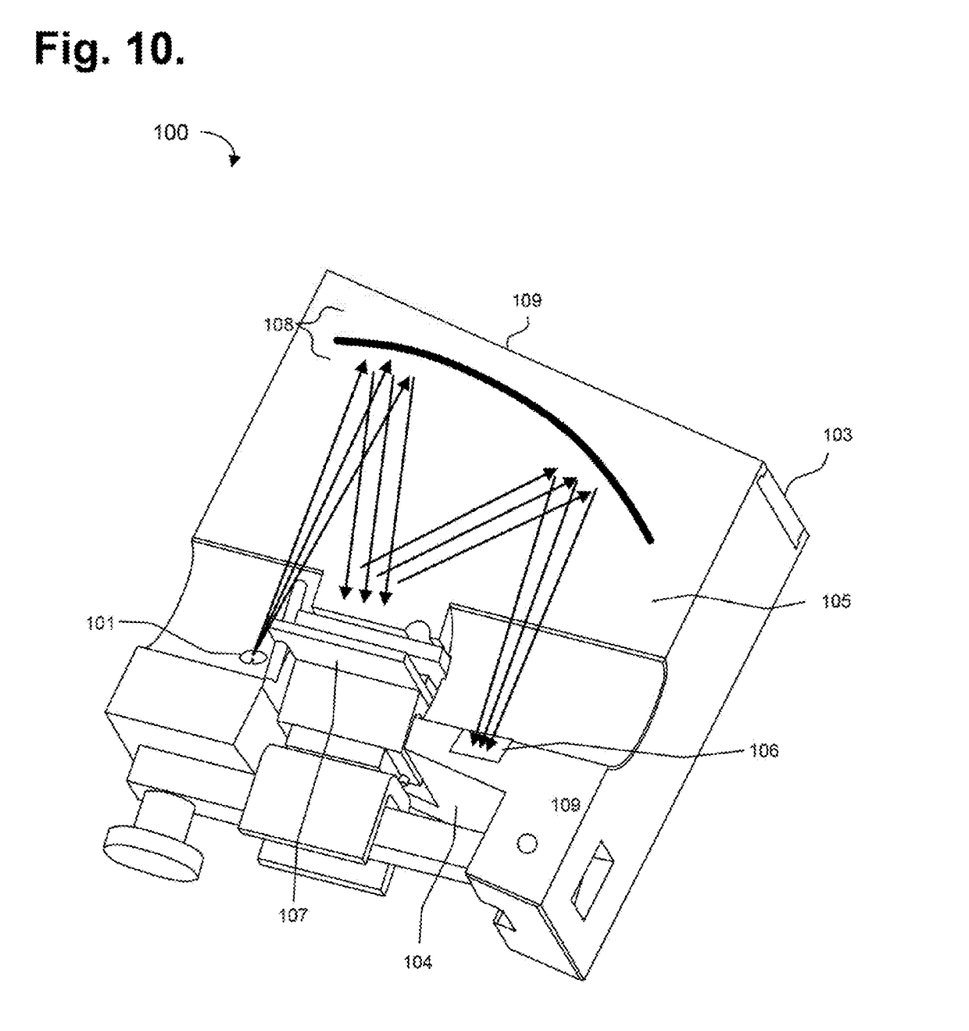
FIG. 10 is a block diagram showing, by way of example, a cross-section of a parallel surface plasmon resonance coupler and disperser sensor.

A housing can conformably surround the optical components to generate a parallel SPRCD sensor for convenient use and portability. FIG. 10 is a block diagram showing a cross-section of a parallel SPRCD sensor 100. A housing 109 can surround the optical components and can be made of plastic, such as epoxy. Alternatively, the optical components can also be fixed to an optical bench made of metal or plastic material. The optical bench can include a substantially flat layer of the material upon which the optical components are affixed. Other types of materials for the housing and optical bench can be used. The light source 101 and detector 106 can be located within the housing 109 on a sensor side 104 opposite the optical board 108, which is located on an optic side 103. In a further embodiment, the light source 101 and detector 106 can be affixed to a sensor board (not shown), which is located on the sensor side 104. The light source 101 and the detector 106 of the sensor board can face the one or more mirrors affixed to the optical board 108 of the optical side 103.

A sample side 105 of the housing can be located between the optic 103 and sensor 104 sides. The sample side 105 can include a sample opening configured to removably receive an SPRCD cartridge or sensor element. Alternatively, the sample opening can be positioned in the sensor side 104 or optical side 103. The SPRCD cartridge or sensor element can be permanently or removably situated in the sample opening and held in place using a pressure distributing metal layer, as described above with respect to FIG. 7. The SPRCD cartridge can include an optic window cover and the sensor element having a metal layer with immobilized biorecognition elements. The optic window cover can be also integrated in the sensor housing as a part of the sample opening. One or more microfluidic channels can be formed directly in the optical window cover, directly in the sensor element, or can be produced by affixing shaped gaskets, laser-etched foil or mechanically cut channels between the SPCRD chip and the optical window cover. The gaskets can be formed from polyester or vinyl, and the foil layer can include self-adhesive layer. Other gaskets and foils could be used. To form the SPRCD cartridge, the optic window cover is placed on top of the sensor element 107 with the microfluidic channels located between the sensor element and optic window cover.

An input port is formed at an opening in the optic window cover or in the sensor element 107 at the beginning of each microfluidic channel. Each input port is configured to receive a sample tube. The microfluidic channels can end at a common output port, which is formed as an opening in the optic window cover or the sensor element. Alternatively, an output port can be provided for each microfluidic channel. The output port is configured to receive a waste tube for disposing of a sample. Once formed, the SPRCD cartridge is loaded into the cartridge holder, which can include two C-shaped brackets configured to receive the cartridge and affixed to a cross bar.

A further embodiment includes direct attachment of the sensor element into the SPRCD sensor. The optic window cover can be mounted either to the sensor board or to the optical board as a part of the sensor element reception slot. Once the SPRCD cartridge or the removable sensor element is aligned in the slot, the sample tubes are properly inserted into the input ports and the waste tube is inserted into the output port. The sample tubes are secured by a sealing. O-ring placed around each sample tube, as described above with respect to FIG. 7.

Once the SPRCD cartridge or SPRC element is inserted, a rubber layer can sit upon the optic window cover. Above the rubber layer sits a pressure distributing metal layer. Another pressure distributing layer is located at the back of the sensor element and applies an equally distributed force on the sensor element surface in normal direction. The sample tubes originate and the waste tube ends in slots through one of these pressure distributing elements. The sample tubes extend along a top surface of the pressure distributing metal layer to which they are mounted and then down through the pressure distributing metal layer to be received by the input port of the SPRCD cartridge or the optic window cover. The waste tube originates at the output port and extends up through the pressure distributing metal layer, out of which the waste tube exits. In one embodiment, there are four sample tubes, which are each received by an input port connected to a microfluidic channel.

Once the sensor element or the whole SPRCD cartridge is in place, a user can apply a sample containing a particular analyte to each input tube. The liquid sample can be pumped through the sample tube using a peristaltic pump or using another type of a pump, or liquid sample delivery system. Other pumps and liquid delivery systems are possible. The sample flows through the input tube to the microfluidic channel. Biorecognition elements can be immobilized on the metal layer of the sensor element. As the sample flows through the microfluidic channel, analyte from the sample may bind the biorecognition elements based on their binding affinity. The sample ends at a common output port from which the waste tube extends. The parallel SPRCD sensor continuously collects spectra of the diffracted optical wave from the individual microfluidic channels and calculates the resonant wavelengths, which produce a sensor response from all channels in real time.

In a further embodiment, the housing can include a USB port for transmitting the collected data, which is translated into an electric signal for transferring to a USB host.

While the invention has been particularly shown and described as referenced to the embodiments thereof, those skilled in the art will understand that the foregoing and other changes in form and detail may be made therein without departing from the spirit and scope of the invention.

What is claimed is:

1. A surface plasmon resonance coupler and disperser system, comprising:
   a light source emitting an optical wave through a collimating element;
   a sensor element facing the light source and comprising a diffraction grating having a periodically modulated surface to receive the optical wave directly projected from the light source and to simultaneously excite surface plasmons and disperse the optical wave via diffraction; and
   a detector facing the diffraction grating and in receipt of the diffracted optical wave that is diffracted off the sensor element to determine a wavelength spectrum of the diffracted optical wave that is coupled to the surface plasmons by measuring the spatial distribution of intensity of the diffracted optical wave, wherein the detector is located at a distance from the sensor element, which is determined by at least one of an angular separation of diffracted wavelength components, a wavelength spectrum of the incident optical wave, and a diameter of the incident optical wave.

2. A surface plasmon resonance coupler and disperser system according to claim 1, wherein the collimating element comprises at least one of a parabolic mirror, spherical mirror, toroidal mirror, spherical lens and aspheric lens.

3. A surface plasmon resonance coupler and disperser system according to claim 1, further comprising:
   a lens diaphragm positioned in line with the light source and the sensor element and comprising at least one of a circular and rectangular shape.

4. A surface plasmon resonance coupler and disperser system according to claim 1, wherein the collimating element and the diaphragm are provided as a single device.

5. A surface plasmon resonance coupler and disperser system according to claim 1, wherein the detector is positioned at an angle measured from the sensor element.

6. A surface plasmon resonance coupler and disperser system according to claim 1, wherein the periodically modulated surface of the sensor element is covered with a metal layer.

7. A surface plasmon resonance coupler and disperser system according to claim 6, wherein the metal layer comprises one of gold and silver.

8. A surface plasmon resonance coupler and disperser system according to claim 6, wherein the metal layer is covered by a layer comprising biorecognition elements capable of interaction with chemical and biological species.

9. A surface plasmon resonance coupler and disperser system according to claim 1, wherein the periodically modulated surface of the diffraction grating comprises sinusoids.

10. A surface plasmon resonance coupler and disperser system according to claim 1, wherein the detector comprises at least one of a charge coupled device, a photo-diode array, and a complimentary metal-oxide semiconductor detector.

11. A surface plasmon resonance coupler and disperser system according to claim 1, wherein the light source comprises at least one of a light emitting diode, filament lamp, discharge lamp, and superluminescent diode.

12. A surface plasmon resonance coupler and disperser system, comprising:
   a light source emitting an optical wave;
   a sensor element comprising a diffraction grating having a periodically modulated surface to receive the optical wave and to simultaneously excite surface plasmons and disperse the optical wave via diffraction;
   a detector placed co-planar to the light source and in receipt of the optical wave, which is diffracted off the sensor element, wherein the sensor element is positioned between the light source and the detector; and
   a single mirror comprising a concave reflective surface facing each of the light source, sensor element, and detector, and contoured to reflect the optical wave from the light source onto the periodically modulated surface of the diffraction grating and to further reflect the diffracted optical wave from the diffraction grating onto the detector.

13. A surface plasmon resonance coupler and disperser system according to claim 12, wherein the detector comprises at least one of a charge coupled device, a photo-diode array, and a complimentary metal-oxide semiconductor detector.

14. A surface plasmon resonance coupler and disperser system according to claim 12, wherein the light source comprises at least one of a light emitting diode, filament lamp, discharge lamp, and superluminescent diode.

15. A surface plasmon resonance coupler and disperser system according to claim 12, wherein the mirror comprises at least one of a toroidal mirror, a spherical mirror, and a parabolic mirror.

16. A surface plasmon resonance coupler and disperser system according to claim 12, wherein the periodically modulated surface of the diffraction grating is covered by a metal layer.

17. A surface plasmon resonance coupler and disperser system according to claim 16, wherein the metal layer comprises one of gold and silver.

18. A surface plasmon resonance coupler and disperser system according to claim 16, wherein the periodically modulated surface of the diffraction grating is covered by a layer comprising biorecognition elements capable of interaction with chemical and biological species.

19. A surface plasmon resonance coupler and disperser system according to claim 12, wherein the periodically modulated surface of the diffraction grating comprises sinusoids.

20. A surface plasmon resonance coupler and disperser system, comprising:
   a light source to emit an optical wave;
   a sensor element comprising a diffraction grating having a periodically modulated surface to receive the optical wave and to simultaneously excite surface plasmons and disperse the optical wave via diffraction;
   an imaging element comprising a reflective surface and contoured to receive the optical wave that is diffracted off the sensor element and to reflect the incident diffraction of the optical wave;
   a detector in receipt of the incident diffraction reflected by the imaging element; and
   a collimating element positioned in line between the light source and the sensor element and to redirect the optical wave received directly from the light source onto the sensor element, wherein the collimating element and the imaging element are located on an optic board.

21. A surface plasmon resonance coupler and disperser system according to claim 20, wherein the collimating element comprises at least one of a parabolic mirror, spherical mirror, toroidal mirror, spherical lens, and aspheric lens.

22. A surface plasmon resonance coupler and disperser system according to claim 20, wherein the imaging element comprises at least one of a toroidal mirror, spherical mirror, parabolic mirror, lens, and lens assembly.

23. A surface plasmon resonance coupler and disperser system according to claim 20, wherein the light source comprises at least one of a light emitting diode, filament lamp, discharge lamp, and superluminescent diode.

24. A surface plasmon resonance coupler and disperser system according to claim 20, wherein the detector comprises at least one of a charge coupled device, a photo-diode array, and a complimentary metal-oxide semiconductor detector.

25. A surface plasmon resonance coupler and disperser system according to claim 20, wherein the periodically modulated surface of the diffraction grating is covered by a metal layer.

26. A surface plasmon resonance coupler and disperser system according to claim 25, wherein the metal layer comprises one of gold and silver and further wherein the periodically modulated surface comprises sinusoids.

27. A surface plasmon resonance coupler and disperser system according to claim 25, wherein the metal layer is covered by a layer comprising biorecognition elements capable of interaction with chemical and biological species.

* * * * *